United States Patent [19]
Tung et al.

[11] Patent Number: 5,912,269
[45] Date of Patent: *Jun. 15, 1999

[54] BUTYRATE PRODRUGS DERIVED FROM LACTIC ACID

[75] Inventors: Roger D. Tung, Cambridge; Biqin Li, Bedford, both of Mass.

[73] Assignee: Vertex Pharmaceuticals, Inc., Cambridge, Mass.

[21] Appl. No.: 08/640,260

[22] Filed: Apr. 30, 1996

[51] Int. Cl.$^6$ .................................................. A01N 37/02
[52] U.S. Cl. ........................................................ 514/547
[58] Field of Search .............................................. 514/547

[56] References Cited

U.S. PATENT DOCUMENTS

| | | |
|---|---|---|
| 3,526,518 | 9/1970 | Kleiman . |
| 4,479,957 | 10/1984 | Cullinan et al. . |
| 5,196,136 | 3/1993 | Dishart et al. . |
| 5,454,806 | 10/1995 | Shinonome . |
| 5,569,675 | 10/1996 | Rephaeli et al. ............ 514/547 |

FOREIGN PATENT DOCUMENTS

| | | |
|---|---|---|
| 824041 | 12/1951 | Germany . |
| 45-70000140 | 1/1970 | Japan . |
| 1197012 | 1/1970 | United Kingdom . |

OTHER PUBLICATIONS

Wurtz. Ann Chin (Paris) (3) (59) (1860) 177 Berlstein Pry # 71662-27-6.

Abraham Nudelman et al., "Novel Anticancer Prodrugs of Butyric Acid," *J. Med. Chem.*, vol. 35, pp. 694–704 (1992).

Harold L. Newmark and Charles W. Young, "Butyrate and Phenylacetate as Differentiating Agents: Practical Problems and Opportunities," *J. Cell. Biochem.*, vol. 22, pp. 247–253 (1995).

Zi–Xing Chen and Theodore R. Breitman, "Tributyrin: A Prodrug of Butyric Acid for Potential Clinical Applicaton in Differentiation Therapy," *Cancer Research*, vol. 54, pp. 3494–3499 (1994).

Antonius A. Miller et al., "Clinical Pharmacology of Sodium Butyrate iin Patients with Acute Leukemia," *Eur. J. Clin. Oncol.*, vol. 23, No. 9, pp. 1283–1287 (1987).

Anne F. Collins et al., "Oral Sodium Phenylbutyrate Therapy in Homozygous β–Thalassemia: A Clinical Trial," *Blood*, vol. 85, pp. 43–49 (1995).

Charles Chany and Italina Cerutti, "Antitumour Effect of Arginine Butyrate in Conjunction with Corynebacterium Parvum and Interferon," *Int. J. Cancer*, vol. 30, pp. 489–493 (1982).

Philippe Pouillart et al., "Pharmacokinetic Studies of N–Butyric Acid Mono–and Polyesters Derived from Monosaccharaides," *J. Pharm. Sci.*, vol. 81, No. 3, pp. 241–244 (1992).

Michiro Otaka et al., "Antibody–Mediated Targeting of Differentiation Inducers to Tumor Cells: Inhibition of Colonic Cancer Cell Growth in Vitro and In Vivo, A Preliminary Note," *Biochem. Biophy. Res. Comm.*, vol. 158, No. 1, pp. 202–208 (1989).

Abraham Novogrodsky et al., "Effect of Polar Organic Compounds on Leukemic Cells: Butyrate–Induced Partial Remission of Acute Myelogenous Leukemia in a Child," *Cancer*, vol. 51, No. 1, pp. 9–14, (1983).

O.C. Velazquez et al., "Butyrate and the Colonocyte: Implications for Neoplasia," *Dig. Dis. Sci.*, vol. 41, pp. 727–739 (1996).

A. Hague et al., "Apoptosis in Colorectal Tumour Cells: Induction by the Short Chain Fatty Acids Butyrate, Propionate and Acetate and by the Bile Salt Deoxycholate," *Int. J. Cancer*, vol. 60, pp. 400–406 (1995).

K.N. Prasad, "Butyric Acid: A Small Fatty Acid with Diverse Biological Functions," *Life Sci.*, vol. 27, pp. 1351–1358 (1980).

Bar–Zeev, M., et al., "Laboratory Evaluation of Tick Repellents," *J. Med. Ent.*, vol. 10, pp. 71–74 (1973).

Blau, C.A.., et al., "Fetal Hemoglobin Induction with Butyric Acid: Efficacy and Toxicity", *Chemical Abstracts*, 118:116458 (*Blood*, 81(2), pp. 529–537 (1993).

Liakopoulou, E., et al., "Stimulation of Fetal Hemoglobin Production by Short Chain Fatty Acids", *Chemical Abstracts* 123:281728 (*Blood*, 86(8), pp. 3227–35 (1995).

Okumura, K., et al., "Synthesis and Hypocholesterolemic Activities of Eritadenine Derivatives," *J. Med. Chem.*, vol. 17, pp. 846–855 (1974).

Sebti, S., et al., "A Convenient Conversion of 2–Acyloxy–3–chlorocarboxamides to 3–Acyloxy–2–azetidinones in Heterogeneous Media," *Synthesis*, vol. 7, pp. 546–549 (1983).

Showa, "Acyloxyacetic Acid Derivatives," CA 102:166,475, Abstract of JP 59190952 A2 (1985).

*Primary Examiner*—Paul J. Killos
*Attorney, Agent, or Firm*—Fish & Neave; James F. Haley, Jr.; Margaret A. Pierri

[57] ABSTRACT

This invention relates to butyrate prodrugs derived from lactic acid and pharmaceutical compositions and methods employing them, either alone or in combination with other agents, for increasing gamma globin and fetal hemoglobin in a patient. These compounds, compositions and methods are particularly effective in treating β-hemoglobinopathies, including sickle cell syndromes and β-thalassemia syndromes. In addition, this invention relates to the use of these prodrugs, alone or in combination with other agents, to stimulate cell differentiation which prevents proliferation of malignant cells. These methods are particularly useful in treating cancer, especially malignant hematological disorders.

12 Claims, 1 Drawing Sheet

5,912,269

BUTYRATE PRODRUGS DERIVED FROM LACTIC ACID

TECHNICAL FIELD OF THE INVENTION

This invention relates to butyrate prodrugs derived from lactic acid and pharmaceutical compositions and methods employing them, either alone or in combination with other agents, for increasing gamma globin and fetal hemoglobin in a patient. These compounds, compositions and methods are particularly effective in treating β-hemoglobinopathies, including sickle cell syndromes and β-thalassemia syndromes. In addition, this invention relates to the use of these prodrugs, alone or in combination with other agents, to stimulate cell differentiation which prevents proliferation of malignant cells. These methods are particularly useful in treating cancer, especially malignant hematological disorders.

BACKGROUND OF THE INVENTION

β-hemoglobinopathies are a group of inherited disorders of β-globin biosynthesis. Although efforts have concentrated on a variety of therapeutic regimens, feasible clinical treatments for these debilitating diseases remain scarce.

Various therapies have been utilized in the treatment of β-hemoglobinopathies, each accompanied by drawbacks. G. P. Rogers et. al., "Current and Future Strategies for the Management of Hemoglobinopathies and Thalassemia", *Hematology* 1994, *Education Program American Society of Hematology*, pp. 9–20 (1994). Although the chemotherapeutic agent hydroxyurea stimulates fetal hemoglobin production and reduces sickling crisis in sickle cell anemia patients, its use in monotherapy is potentially limited by myelotoxicity and the risk of carcinogenesis. Potential long term carcinogenicity is also a drawback of 5-azacytidine-based therapies. Red blood cell transfusions expose patients to the potential of a wide range of infectious viral agents, as well as alloimmunization. Bone marrow transplants are not a readily available option for a large number of patients. Erythropoietin-based therapies have not proved consistent among a range of patient populations. Such varying drawbacks contraindicate the long term use of such agents or therapies.

It is clear from multicenter studies involving numerous patients with sickle cell disease that increased blood levels of fetal hemoglobin are associated with lower events of sickle cell crisis and longer survival time [O. S. Platt et al., "Pain in Sickle Cell Disease, *New Eng. J. Med.*, 325, pp. 11–16 (1991); O. S. Platt et al., "Mortality ion Sickle Cell Disease", *New Eng. J. Med.*, 330, pp. 1639–44 (1994)]. Accordingly, in an effort to avoid the disadvantages of conventional therapies for β-hemoglobinopathies, therapies have centered around ways to increase fetal hemoglobin production. Recent clinical trials have used butyrate analogs, including arginine butyrate and isobutyramide, to stimulate fetal hemoglobin production as a means of treatment [S. Perrine et al., A Short Term Trial of Butyrate to Stimulate Fetal-Globin-Gene Expression in the β-globin Disorders", *N. Eng. J. Med.*, 328, pp. 81–86 (1993); S. P. Perrine et. al., "Isobutyramide, an Orally Bioavailable Butyrate Analogue, Simulates Fetal Globin Gene Expression In Vitro and In Vivo", *British J. Haematology*, 88, pp. 555–61 (1994); A. F. Collins et al., "Oral Sodium Phenylbutyrate Therapy in Homozygous βThalassemia: A Clinical Trial", *Blood*, 85, pp. 43–49 (1995).

Following the observation that butyric acid induces cell differentiation in vitro [A. Leder and P. Leder, "Butyric Acid, a Potent Inducer of Erythroid Differentiation in Cultured Erythroleukemic Cells", *Cell*, 5, pp. 319–22 (1975)], that compound was found to demonstrate promising effects in leukemia patients, by inducing cell differentiation [A. Novogrodsky et al., "Effect of Polar Organic Compounds on Leukemic Cells", *Cancer*, 51, pp. 9–14 (1983)]. Aside from their use in treating β-hemoglobinopathies, butyrate derivatives such as arginine butyrate, an arginine salt of butyric acid, have been shown to exert anti-tumor and anti-leukemia effects in mice [C. Chany and I. Cerutti, "Antitumor Effect Of Arginine Butyrate in Conjunction with Corynebacterium Parvum and Interferon", *Int. J. Cancer*, 30, pp. 489–93 (1982); M. Otaka et al., "Antibody-Mediated Targeting of Differentiation Inducers To Tumor Cells: Inhibition of Colonic Cancer Cell Growth in vitro and in vivo", *Biochem. Biophys. Res. Commun.*, 158, pp. 202–08 (1989)].

Although butyrate salts have the advantage of low toxicity as compared with conventional chemotherapeutic agents, their short half-lives in vivo have been viewed as a potential obstacle in clinical settings [A. Miller et al., "Clinical Pharmacology of Sodium Butyrate in Patients with Acute Leukemia", *Eur. J. Clin. Oncol.*, 23, pp. 1283–87 (1987); Novogrodsky et al., supra]. The rapid clearance of these agents results in an inability to deliver and maintain high plasma levels of butyrate which necessitates administration by intravenous infusion. Another potential obstacle to the use of butyrate salts is salt overload and its physiological sequelae.

In view of these observations, various prodrugs of butyric acid have been proposed for use in β-hemoglobinopathy and leukemia differentiation therapies. Such prodrugs include tributyrin and n-butyric acid mono- and polyesters derived from monosaccharides [Z. Chen and T. Breitman, "Tributyrin: A Prodrug of Butyric Acid for Potential Clinical Application in Differentiation Therapy", *Cancer Res.*, 54, pp. 3494–99 (1994); H. Newmark et al., "Butyrate as a Differentiating Agent: Pharmacokinetics, Analogues and Current Status", *Cancer Letts.*, 78, pp. 1–5 (1994); P. Pouillart et al., "Pharmacokinetic Studies of N-Butyric Acid Mono- and Polyesters Derived From Monosaccharides", *J. Pharm. Sci.*, 81, pp. 241–44 (1992)]. Such prodrugs have not proved useful as therapeutics, however, due to factors such as short half-life, low bioavailability, low $C_{max}$, or lack of effective oral deliverability. Other prodrugs, such as AN-9 and AN-10 [A. Nudelman et al., "Novel Anticancer Prodrug of Butyric Acid", *J. Med. Chem.*, 35, pp. 687–94 (1992)], elicit metabolites that may produce formaldehyde in vivo, leading to toxic effects in patients.

To date, conventional methods and therapeutic agents have not proved to be safe and effective for all patients in the treatment of β-hemoglobinopathies. This is also the case for diseases characterized by neoplastic, tumorigenic or malignant cell growth, or malignant hematological disorders. Accordingly, the need exists for alternatives having advantages over, and avoiding the disadvantages of, such conventional methods and agents, while providing effective therapy for those target diseases.

DISCLOSURE OF THE INVENTION

The present invention solves these problems by providing butyrate prodrugs of lactic acid and pharmaceutical compositions comprising them. These butyrate prodrugs demonstrate good bioavailability, effective oral deliverability, good half-life and surprisingly high $C_{max}$.

When administered to a patient, the butyrate prodrugs in these compositions release butyrate more efficiently than prior art butyrate prodrugs. This produces a higher plasma level of butyrate relative to the amount of prodrug administered as compared to the prior art butyrate prodrugs.

Butyrate released from these prodrugs increase gamma globin synthesis, increase red blood cell hydration and stimulate cell differentiation. Increased gamma globin synthesis causes an increase in fetal hemoglobin formation which, in turn, increased the oxygen carrying capacity of red blood cells and prevents sickling. Increased hydration of red blood cells also prevents sickling. The ultimate result of these cascades is the increased survival of red blood cells.

This makes the pharmaceutical compositions of this invention particularly useful in methods for treating β-hemoglobinopathies, including sickle cell syndromes and β-thalassemia syndromes.

In addition, the ability of the butyrate prodrugs of this invention to stimulate cell differentiation has an antiproliferative effect on malignant cells, particularly malignant hemopoietic cells. Thus, the compounds and pharmaceutical compositions of this invention may be employed in methods for treating cancer, particularly malignant hematological disorders.

Because a patient can be treated with lower doses of the present prodrugs in order to achieve a desired serum butyrate concentration, toxicity associated with the non-butyrate portion of the prodrug is less of a concern.

All of these features facilitate the chronic therapy regimens often prescribed for patients suffering from β-hemoglobinopathies or cancer. At the same time, they also facilitate convenient dosing schemes for and patient compliance with such therapy regimens. Furthermore, the methods and compositions of this invention are not beset by the variety of side effects which typically characterize conventional therapy regimens.

DETAILED DESCRIPTION OF THE INVENTION

Definitions

Figure 1:
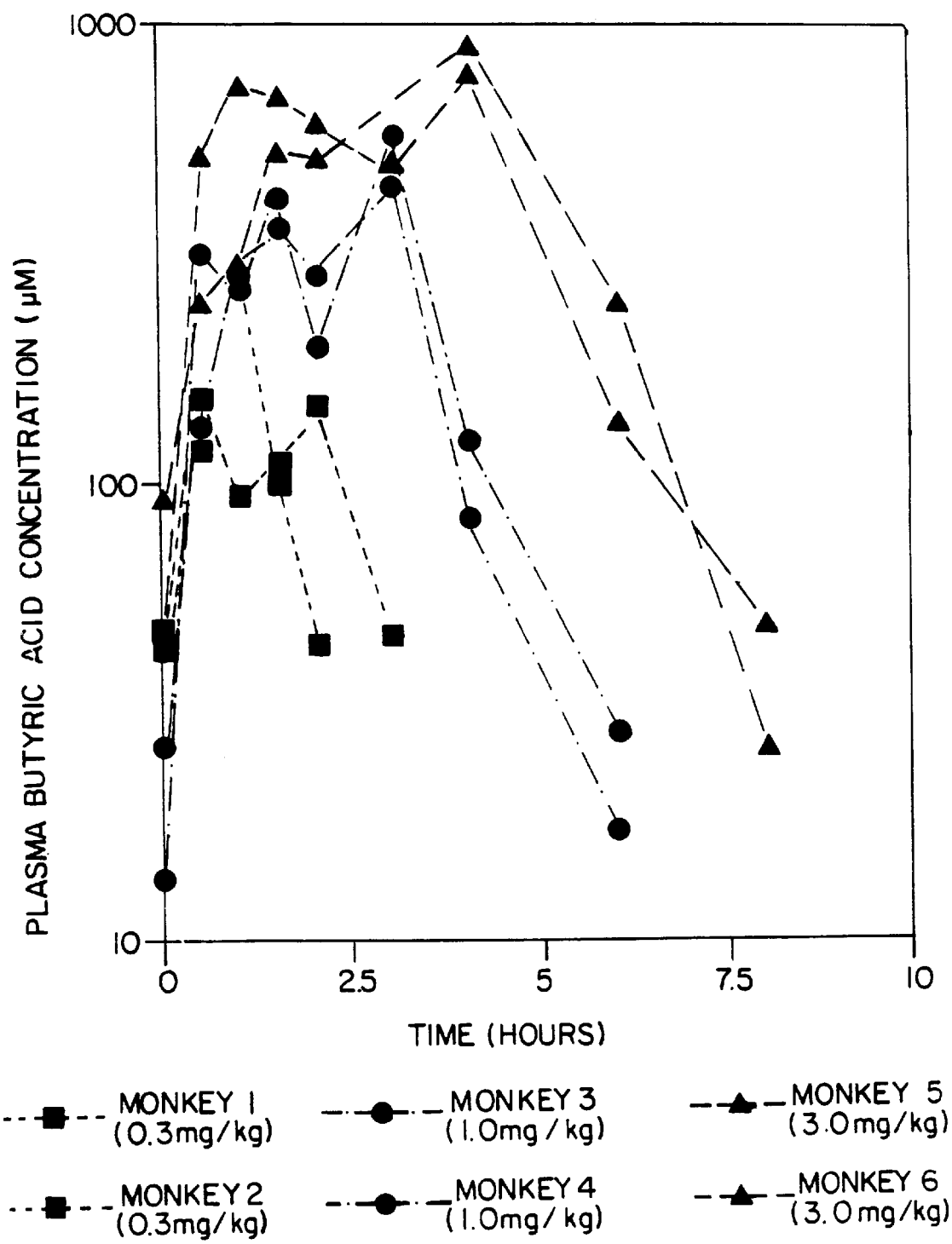
FIG. 1 depicts the time course of plasma butyric acid concentration following administration of the various doses of compound IIIc in individual monkeys.

The following definitions are used throughout the application.

As used herein, the term "alkyl", alone or in combination with any other term, refers to a straight-chain or branched-chain aliphatic hydrocarbon radical containing the specified number of carbon atoms, or where no number is specified, preferably from 1 to 10 carbon atoms, which may contain one or more unsaturated bonds. Examples of alkyl radicals include, but are not limited to, methyl, ethyl, isopropyl, butyl, pentyl and the like. The term "alkyl", as used herein also includes the terms "alkenyl" and "alkynyl", which are defined below.

The term "alkenyl", alone or in combination, refers to a straight-chain or branched-chain alkenyl radical containing 2 to 10 and more preferably from 2 to 6 carbon atoms. Examples of alkenyl radicals include, but are not limited to, vinyl, allyl, E-propenyl, Z-propenyl, E,E-hexadienyl, E,Z-hexadienyl, Z,Z-hexadienyl and the like.

The term "alkynyl", alone or in combination, refers to a straight-chain or branched chain alkynyl radical containing from 2 to 10 and more preferably from 2 to 6 carbon atoms.

Examples of such radicals include, but are not limited to, ethynyl (acetylenyl), propynyl, propargyl, butynyl, 1,4-hexydiynyl, decynyl and the like. "Alkynyl", as used herein, also refers to radicals containing both carbon-carbon double bonds and carbon-carbon triple bonds, such as Z-pent-2-en-4ynyl.

The term "carbocyclyl", alone or in combination with any other term, refers to a carbocyclic radical, which may be saturated, partially unsaturated or aromatic, containing the specified number of carbon atoms, preferably from 3 to 14 carbon atoms and more preferably from 5 to 10 carbon atoms. The term "carbocyclic" as defined include radicals of "cycloalkyls", "cycloalkenyls" and carbocyclic "aryls". Carbocyclyl also refers to radicals containing several carbocyclic rings, which are fused or spiro-fused, comprising from 4 to 14 carbon atoms.

The term "cycloalkyl", alone or in combination, refers to a cyclic alkyl radical containing from 3 to 8, preferably from 3 to 6, carbon atoms. Examples of such cycloalkyl radicals include, but are not limited to, cyclopropyl, cyclobutyl, cyclopentyl, cyclohexyl and the like.

The term "cycloalkenyl", alone or in combination, refers to a cyclic alkyl radical containing from 4 to 8, preferably from 5 to 6, carbon atoms and one or more double bonds. Examples of such cycloalkenyl radicals include, but are not limited to, cyclopentenyl, cyclohexenyl, cyclopentadienyl and the like.

The term "heterocyclyl" refers to a carbocyclyl, preferably of 5 to 7 atoms, containing from 1–4 heteroatoms independently selected from oxygen, nitrogen and sulfur in place of an equal number of carbon atoms. That term also refers to substituted or unsubstituted, 8–11 membered bicyclic ring systems, which may be aromatic or non-aromatic containing in either or both rings from 1–4 heteroatoms independently selected from oxygen, nitrogen and sulfur and wherein the terms nitrogen and sulfur may include any oxidized form of nitrogen and sulfur and the quarternized form of any basic nitrogen. A heterocyclyl group may be connected to a structure through any atom of the group which results in a stable chemical bond.

Examples of non-aromatic heterocyclic radicals include, but are not limited to, 2-pyrrolinyl, 3-pyrrolinyl, 1,3-dioxolyl, 2H-pyranyl, 4H-pyranyl, piperidyl, 1,3-dioxanyl, 1,4-dioxanyl, morpholinyl, 1,4-dithianyl, thiomorpholinyl, thiomorpholinyl sulfone, tetrahydrofuryl, piperazinyl and quinuclidinyl.

Examples of aromatic heterocyclic radicals include, but are not limited to, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl and the like.

The term "aryl" refers to an aromatic carbocyclic group, preferably of 6 atoms, or an 8–14 membered aromatic polycyclic aromatic ring system;

Examples of "aryl" groups, include, but are not limited to, phenyl, 1-naphthyl, 2-naphthyl, indenyl, azulenyl, fluorenyl and anthracenyl.

When substituted, each "carbocyclyl" and "heterocyclyl" may independently contain one to three substituents that are independently selected from hydroxy; halogen; C(1–6)-straight or branched alkyl, alkylamino or alkoxy; C(2–6)-straight or branched alkenyl, alkenylamino, alkynylamino, alkynyl, alkenoxy or alkynoxy; nitro, NH₂; thiol; alkylthio; carbocyclyl; carbocyclylalkyl; carbocyclylalkenyl; carbocyclylalkynyl; heterocyclyl; heterocyclylalkyl; heterocyclylalkenyl; heterocyclylalkynyl; methylenedioxy; carboxamido; alkylcarbonylamino; carbocyclylcarbonylamino; heterocyclylcarbonylamino; carbocyclylalkylcarbonylamino; heterocyclylalkylcarbonylamino; sulfonamido; alkylsulfonamido; alkenylsulfonamido; alkynylsulfonamido; and arylsulfonamido. The substituents listed above may be attached to either a ring carbon atom or a ring heteroatom.

The term "alkoxy" refers to an O—C(1–6)-straight or branched alkyl radical. Examples of alkoxy radicals include, but are not limited to, methoxy, ethoxy, n-propoxy, iso-propoxy, n-butoxy, isobutoxy, sec-butoxy and tert-butoxy.

The term "alkenoxy" refers to an O—C(2–6)-straight or branched alkenyl radical. Examples of alkenoxy radicals include, but are not limited to, allyloxy, E and Z-3-methyl-2-propenoxy.

The term "alkynoxy" refers to an O—C(2–6)-straight or branched alkynyl radical. Examples of alkenoxy radicals include, but are not limited to, propargyloxy and 2-butynyloxy.

The term "alkylamino" refers to a C(1–6)-straight or branched alkyl-NH radical or a C(1–6)-straight or branched alkyl-N—C(1–6)-straight or branched alkyl radical where the alkyl radicals may be the same or different. Examples of suitable alkylamino radicals include, but are not limited to, methylamino, ethyl amino, propylamino, isopropyl amino, t-butyl amino, N,N-diethylamino and N,N-methylethylamino.

The term "alkenylamino" refers to a C(2–6)-straight or branched alkenyl-NH radical, a C(2–6)-straight or branched alkenyl-N—C(1–6)-straight or branched alkyl radical, or a C(2–6)-straight or branched alkenyl-N—C(2–6)-straight or branched alkenyl radical where the alkenyl radicals may be the same or different. An example of a suitable alkenyl amino radical is, but is not limited to, allylamino. Alkenylamino also refers to The term "alkynylamino" refers to a C(3–6)-straight or branched alkynyl-NH radical, a C(3–6)-straight or branched alkynyl-NH—C(1–6)straight or branched alkyl radical, a C(3–6)-straight or branched alkynyl-NH—C(2–6)straight or branched alkenyl radical, or a C(3–6)-straight or branched alkynyl-N—C(3–6)-straight or branched alkynyl radical where the alkynyl radicals may be the same or different. An example of a suitable alkynyl amino radical is, but is not limited to, propargylamino and the like.

The term "amido" refers to a —C(O)NH₂ radical.

The term "alkylamido" refers to a —C(O)NH—C(1–6)-straight or branched chain alkyl radical or a —C(O)N-[C(1–6)₂-straight or branched chain alkyl radical, wherein the two C(1–6)-straight or branched alkyl chains may be the same or different.

The term "alkylsulfonamido" refers to a C(1–6) straight or branched chain alkyl-S(O)₂NH— radical. An example of alkylsulfonamido is ethanesulfonamido.

In order that the invention herein described may be more fully understood, the following detailed description is set forth.

The compounds of this invention are butyrate prodrugs derived from lactic acid, which are represented by the Formula I:

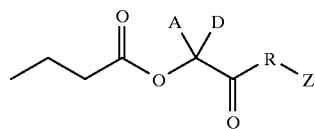

wherein A and D are independently selected from the group consisting of hydrogen, alkoxyalkyl, carbocyclylalkoxyalkyl or C(1–4)-straight or branched alkyl, C(2–4)-straight or branched alkenyl or alkynyl, which may be independently substituted with hydroxy, alkoxy, carboxyalkyl, alkylamido, arylamido, heterocyclylamido, aralkylamido, heterocyclylalkylamido, alkoxycarbonylamino, alkenoxycarbonylamino, carbocyclyloxycarbonylamino, heterocyclyloxycarbonylamino, carbocyclylalkoxycarbonylamino, heterocyclylalkoxycarbonylamino, alkoxyalkoxycarbonylamino, amino, amido, carboxyl, thiol, thioalkyl, thiophenyl, aryl and heterocyclyl; provided that A and D are not simultaneously hydrogen;

R is O, NH, NC(1–5)-straight or branched alkyl or NC(2–5)-straight or branched alkenyl, any of which may be optionally substituted with a carbocyclyl or heterocyclyl moiety;

Z is hydrogen, C(1–4)-straight or branched alkyl, C(2–4)-straight or branched alkenyl or alkynyl, carbocyclyl, or heterocyclyl, any of which may be optionally substituted with 1 or 2 groups independently chosen from C(1–3)-alkyl, C(2–3)-alkenyl or alkynyl, alkoxy, alkenoxy, alkynoxy, amido, thioalkyl, carbocyclyl or heterocyclyl; and each stereogenic carbon may be in the R or S configuration;

provided that said compound is not

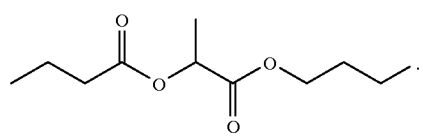

According to a preferred embodiment, D is methyl and A is hydrogen in the compound of Formula I, yielding a compound of formula II:

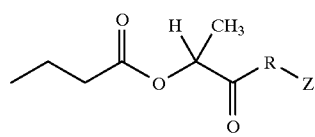

Preferably, in Formula II, R is O, NH, NC(1–3)-alkyl, NC(2–4)-straight or branched alkenyl or N-benzyl and Z is C(1–4)-straight or branched alkyl optionally substituted with one group selected from a 5 to 10-membered carbocyclyl or heterocyclyl. Most preferably, R is O, Z is an unsubstituted C(1–4)-straight or branched alkyl, and the stereochemistry at the methyl-bearing carbon is S.

According to another preferred embodiment, R is oxygen in Formula I, producing a compound of formula III:

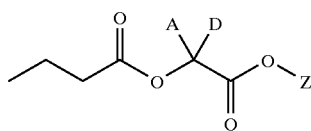

(III)

Preferably, in formula III, A and D are independently selected from hydrogen, methyl, ethyl or allyl; provided that A and D are not both hydrogen; and Z is C(1–3)-alkyl optionally substituted with one group selected from C(5–10)-carbocyclyl or -heterocyclyl.

More preferably, D is hydrogen or methyl, A is unsubstituted C(1–3)-alkyl and Z is unsubstituted C(1–3)-alkyl.

The more preferred pharmaceutical compositions of this invention comprise a compound selected from:

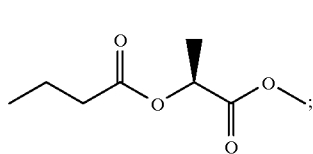

(IIIa)

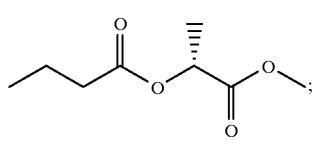

(IIIb)

and

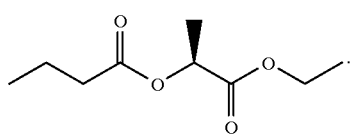

(IIIc)

The most preferred prodrug is compound IIIc.

The prodrugs of Formula I contain one or more asymmetric carbon atoms and thus occur as racemates and racemic mixtures, single enantiomers, diastereomeric mixtures and individual diastereomers. All such isomeric forms of these compounds, as well as mixtures thereof, are included in the pharmaceutical compositions of the present invention.

This invention also encompasses prodrugs of Formula I that are quarternized at any of the basic nitrogen-containing groups. The basic nitrogen can be quarternized with any agents known to those of skill in the art including, for example, lower alkyl halides, such as methyl, ethyl, propyl and butyl chloride, bromides and iodides; dialkyl sulfates, including dimethyl, diethyl, dibutyl and diamyl sulfates; long chain halides, such as decyl, lauryl, myristyl and stearyl chlorides, bromides and iodides; and aralkyl halides, including benzyl and phenethyl bromides. Water or oil-soluble or dispersible products may be obtained by such quarternization.

Prodrugs are hydrolyzed in vivo to release the active ingredient. In the case of the present invention, the disclosed prodrugs release butyric acid. Without being bound by theory, we believe that a threshold concentration of butyric acid in the plasma is required to be maintained for a period of at least several hours during the day over a number of days to induce production of gamma globin chain synthesis and fetal hemoglobin formation, or to induce differentiation in malignant cells, leading to an anticancer effect. The compounds that characterize the compositions of this invention are metabolized in the body in such a way as to produce a high maximal concentration ($C_{max}$) of butyric acid following oral administration. These compounds are also characterized by a sufficiently long half-life ($t_{1/2}$) that ensures good exposure of the patient to butyric acid. Due to the surprising and unexpectedly high $C_{max}$, less of these prodrugs need to administered to produce effective plasma concentration of butyric acid than conventional agents. This, in turn, results in lower potential for toxicity due to the carrier portion of the prodrug, as well as easier administration.

The butyrate prodrugs of this invention may be synthesized by standard organic routes. Many α-hydroxy acids, α-hydroxy esters and α-hydroxy amides are commercially available (e.g., Aldrich Catalog Handbook of Fine Chemicals, 1994–1995). In the case of α-hydroxy esters or α-hydroxy amides, derivatization of the hydroxy group may be carried out using an activated form of butyric acid, such as an acid chloride; symmetrical acid anhydride; mixed carbonic, phosphonic, or sulfonic acid anhydrides; and activated esters such as phenyl, 4-nitrophenyl, pentafluorophenyl, hydroxybenzotriazolyl or N-hydroxysuccinimidyl.

Preferably the derivatization is carried out using a base such triethylamine, diisopropylethylamine, 1,8-diazabicyclo [54.0] undec-7-ene, pyridine or tetramethylguanidine; or aqueous buffers or bases such as sodium carbonate or sodium hydrogen carbonate (see, e.g. E. Haslam, "Recent Development in Methods for the Esterification and Protection of the Carboxyl Group", Tetrahedron, 36, pp. 2409–2433 (1980). Dehydrating agents, such as 1,3-dicyclohexylcarbodiimide or 1-(3-dimethylaminopropyl)-3-ethylcarbodiimide hydrochloride may also be employed. The inclusion of a hyperacylation catalyst, such as 4-dimethylaminopyridine, may improve the efficiency of the reaction (A. Hassner et al., "Direct Room Temperature Esterification of Carboxylic Acids", Tetrahedron Lett., 46, pp. 4475–4478 (1978)). Additional methods are well known in the art and may be readily substituted for those listed above.

If α-hydroxy acids are used, derivatization of the carboxylic acid group may be carried out by first converting the hydroxy group to a butyryl group. This is followed by esterification or amidification of the carboxylic acid, or alternatively by performing a sequence comprising the steps of:

1) transiently blocking the hydroxyl with a removable protecting group;
2) derivatizing the carboxylic acid as an ester or amide;
3) removing the hydroxyl protecting group; and
4) converting the hydroxy group to a butyryl group as above.

The butyrated or hydroxyl-protected α-hydroxy acids may then be converted to their corresponding esters of Formula I (wherein R=O) by carboxyl activation, similar to that described above for butyric acid, followed by reaction with an alcohol in the presence of a suitable base. Reaction of the activated butyrated or hydroxyl-protected α-hydroxy acids with primary or secondary amines yields amines of Formula I (wherein R=NH, N—C(1–5)-straight or branched chain alkyl, or N—C(2–5)-straight or branched chain alkenyl which may be substituted with a carbocyclyl or heterocyclyl moiety). A wide variety of primary, secondary and tertiary alcohols and primary and secondary amines are commercially available or readily produced by methods known in the art. Therefore, this process provides access to compounds of Formula I where R—Z may vary greatly.

Some particularly useful methods for synthesizing compounds of Formula I are shown in Scheme I, below.

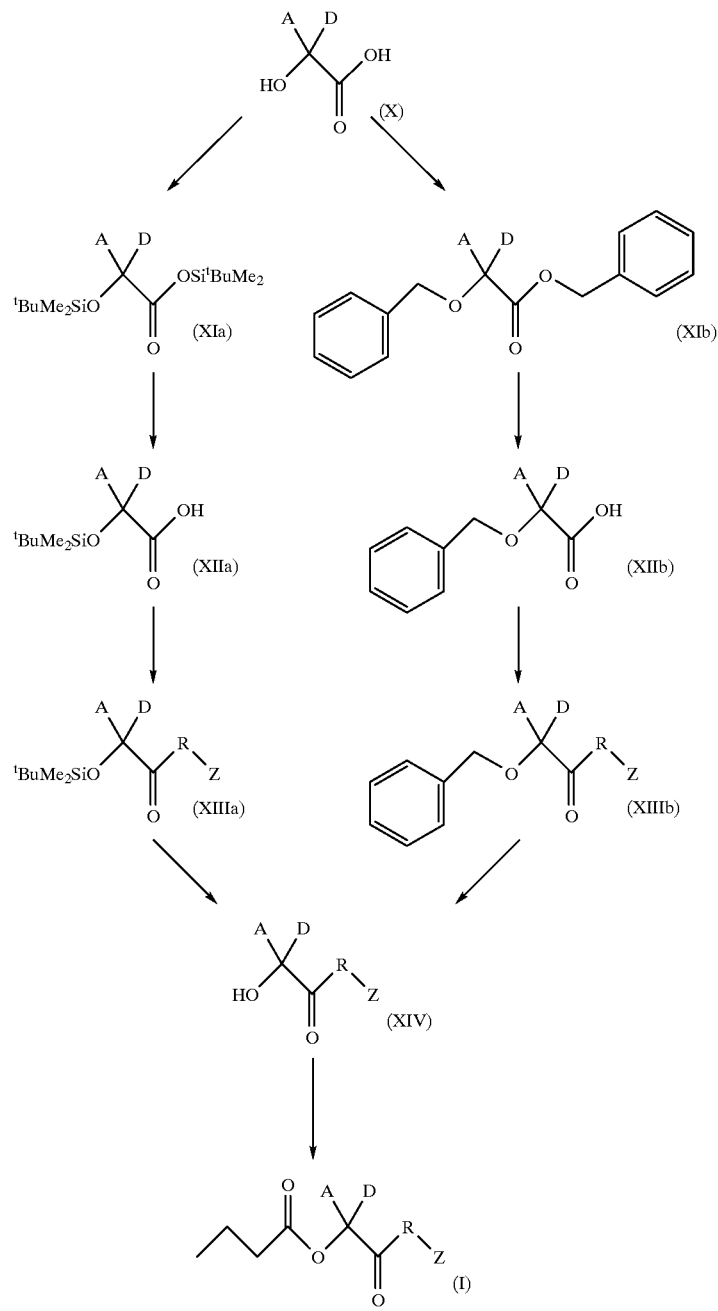

In these methods, the α-hydroxy acid of choice is simultaneously reacted at the hydroxyl and carboxylate groups. Reaction with a suitable silylating reagent, for instance $^t$butyl-dimethylsilyl chloride in the presence of imidazole in dimethyl formamide, yields a bis-silylated compound of Formula XIa or similar silyl derivative. This compound can be converted to a carboxyl-activated derivative by a sequence comprising:

1) partial hydrolysis of carboxyl silyl group, for instance by hydrolysis using about 1 molar equivalent of lithium hydroxide at about −20° C. to about ambient temperature in aqueous dioxane; 2) concentration in vacuo;

3) careful acidification using for instance citric acid;

4) extraction into a suitable organic solvent such as methylene chloride; and 5) carboxyl activation as described above.

Removal of the hydroxyl-protecting silyl group using, for instance, tetrabutylammonium fluoride in tetrahydrofuran at about 0° C. to ambient temperature, or HF-pyridine complex in acetonitrile, yields the hydroxy derivative XIV. Conversion to compounds of Formula I may then be effectuated as described above.

Alternatively, the α-hydroxy acid of Formula X is simultaneously reacted at the hydroxyl and carboxylate groups with an alkyl substituent such as a benzyl derivative as shown in scheme I. Other alkyl derivatives such as allyl, 4-methyloxybenzyl, 2,2,2-trichloroethyl or 2-trimethylsilylethyl may also be used in this step.

The derivatization step may be accomplished by reaction of the compound of Formula X with excess benzyl bromide in the presence of about 2.2–3 equivalents of a strong base, such as sodium hydride, potassium hydride, or potassium 'butoxide, in a suitable inert solvent, such as THF or dimethylformamide, at about −30° C. to about 100° C. depending on the particular α-hydroxy acid and electrophile. Optionally, a phase-transfer catalytic method using a base such as $K_2CO_3$ or NaOH in an inert solvent, such as toluene or acetonitrile, may be used for this alkylation. Suitable catalysts include quartenary ammonium salts, such as $^nBu_4N^+Br^-$, and crown ethers, such as dibenzo-18-crown-6.

Conversion of suitably bis-alkylated compounds of Formula XIb to those of Formula XIIb may be accomplished by saponification, for instance in aqueous methanol or dioxane, using an equimolar or greater amount of alkali metal base, such as hydroxides of sodium, lithium or potassium, at temperature ranging from about −40° C. to about 80° C. Alternatively, reaction with a thiolate anion, such as sodium ethyl thiolate, iodotrimethylsilane or with other ester-deprotecting reagents, will yield the protected carboxylic acid of Formula XIIb (see, e.g., R. C. Larock, "Comprehensive Organic Transformations", pp. 981–985, 1989 VCH Publishers, Inc., New York, N.Y.).

Activation and derivatization similar to that described for compounds of Formula XIIa yield compounds of Formula XIIIb. The benzyl group may be then conveniently removed, e.g., by catalytic hydrogenation using for instance palladium or rhodium metal dispersed on carbon, using a hydrogen source such as hydrogen gas or ammonium formate, or catalytic transfer hydrogenation using cyclohexadiene or the like. Such methods are well known in the art of organic chemistry (see, e.g., P. N. Rylander, "Catalytic Hydrogenation in Organic Synthesis", ©1979 Academic Press, Inc., Orlando, Fla.). Reducing metal methods, involving dissolving the substrate in liquid ammonia and adding an alkali metal, such as metallic sodium, are also known in the art.

If an allyl group is used in place of a benzyl group, its removal may be effectuated by palladium transfer reactions using e.g. tetrakis(triphenylphosphine)Pd$^0$ and an allyl acceptor, such as morpholine or Pd$^{II}$ acetate and $Bu_3SnH$. Methods for employing these and other alcohol protecting groups are described in the art (see, e.g., T. W. Greene and P. G. M. Wuts "Protective Groups in Organic Synthesis", Second Edition ©1991 Academic Press, Inc., Orlando, Fla., pp. 14–120). The resulting compound of Formula XII may then be reacted as described above to produce compounds of Formula I.

α-Hydroxy acids, α-hydroxy esters and α-hydroxy amides, when not commercially available, may conveniently be synthesized by a variety of methods which will be readily apparent to those of skill in the art. For instance, reaction of a glyoxylic acid ester or amide with a suitable carbon-based nucleophile, such as a Grignard reagent, organocuprate or an organolithium reagent, in a suitable inert solvent, such as diethyl ether or tetrahydrofuran, at about −80° C. to about 0° C., will yield a α-hydroxy ester or amide of Formula XIV where A is the nucleophile and D is hydrogen. Similar reactions, carried out on a-ketoesters or amides, yield α, α-disubstituted, α-hydroxyesters or amides (B. M. Trost and I. Fleming, "Comprehensive Organic Syntheses, Vol. I" pp. 49–282 ©1989, PerganLon Press, Oxford, England).

Many α-hydroxy acids may be produced conveniently by reacting the corresponding α-amino acids with a diazetizing agent in a poorly nucleophilic medium. For example, $NaNO_2$ may be added to a solution of an amino acid in aqueous sulfuric acid (R. V. Hoffman et al., "Preparation of (r)-2-Azido Esters from 2-((p-Nitrobenzene)sulfonyl)oxy Esters and Their Use as Protected Amino Acid Equivalents for the Synthesis of Di- and Tripeptides Containing D-Amino Acid Constituents", Tetrahedron Lett., 48, pp. 3007–3020 (1992)). Since numerous α-amino acids may be purchased and many others can be made by known synthetic routes, often in optically active forms, (H. K. Chenault et al., "Kinetic Resolution of Unnatural and Rarely Occurring Amino Acids: Enantioselective Hydrolysis of N-Acyl Amino Acids Catalyzed by Acylase I", J. Am. Chem. Soc., 111, pp. 6354–6364 (1989)), this method provides a ready source of starting materials of formula I.

Alkyl carboxylic acids and their ester and amide derivatives may be converted to α-hydroxy derivatives by formation of an anion at the carbon α to the carboxylate derivative, followed by reaction with an oxygenating agent, such as N-sulfonyl oxaziradines, yield the compound of Formula X or XIV (R. C. Larock, "Comprehensive Organic Transformations", p. 489, ©1989 VCH Publishers, Inc., New York, N.Y.)

Variations of the methods disclosed above and other synthetic approaches known in the literature of synthetic organic chemistry will be apparent to those of ordinary skill in the art. Alternate transient protection and deprotection of reactive groups and their further transformation to produce additional compounds of Formula I, will be readily apparent the skilled artisan.

According to one embodiment, the invention provides a pharmaceutical composition comprising a prodrug of Formula I (including the n-butyl ester specifically excluded from the compounds of this invention) in an amount effective to increase the production of fetal hemoglobin or stimulate cell differentiation in a patient and a pharmaceutically acceptable carrier or adjuvant. More specifically, these compositions are designed to treat a patient suffering from a β-hemoglobinopathy or a malignant disease. The term "malignant disease", as used herein denotes a condition characterized by neoplastic, tumorigenic or malignant cell growth, or a hematological disorder.

An amount effective to increase the production fetal hemoglobin or stimulate cell differentiation in a patient will depend, of course, on the particular disease to be treated, the severity of the disease, the physical condition of the patient and the judgment of the treating physician. Preferably, the prodrug of Formula I will be present in an amount capable of producing a plasma butyric acid concentration of between about 0.03 mM and 3.0 mM within 8 hours of administration. More preferably, the prodrug of formula I is present in an amount that produces a plasma butyric acid concentration of between about 0.1 mM and 1.0 mM within 6 hours of administration. Most preferably, the prodrug in the composition is present in an amount that produces a plasma butyric acid concentration of between about 0.1 mM and 1.0 mM within 2 hours of administration and the concentration remains within that range for at least 2 hours. Dosages of between about 25 mg prodrug/kg body weight and 3 g prodrug/kg body weight administered one or more times per day are capable of producing the desired plasma butyric acid concentration. Preferably, the patient will be administered the prodrug between 1 and 4 times per day.

In a preferred embodiment, these compositions additionally comprise a conventional agent used in the treatment of β-hemoglobinopathies. The conventional agent may be present in the same amount or less than that normally required to treat β-hemoglobinopathies in a monotherapy. The normal dosages of these conventional agents are well known in the art. Such agents include hydroxyurea, clotrimazole, isobutyramide, erythropoietin and salts of short-chain fatty acids, such as phenylacetic acid, phenylbutyric acid and valproic acid. Preferably, the conventional agent used is hydroxyurea.

According to an alternate preferred embodiment, the compositions comprise a butyrate prodrug of this invention and a conventional agent used in the treatment of diseases characterized by neoplastic, tumorigenic or malignant cell growth, or a hematological disorder in a patient. This additional agent may be present in an amount equal to or less than that normally required to treat such diseases in a monotherapy. The normal dosages of these conventional agents are well known in the art. Such agents include, erythropoietin, or cancer chemotherapeutic agents, such as hydroxyurea or 5-azacytidine. Preferably, the conventional agent used is hydroxyurea.

Pharmaceutically acceptable salts of the prodrugs of Formula I (including the n-butyl ester specifically excluded from the compounds of this invention) may also be employed in any of the above-described compositions. Such salts may be derived from pharmaceutically acceptable inorganic and organic acids and bases.

Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids.

Salts derived from appropriate bases include alkali metal (e.g., sodium), alkaline earth metal (e.g., magnesium), ammonium and $N\text{-}(C_{1-4} \text{ alkyl})_4^+$ salts.

The carriers and adjuvants present in the compositions of this invention include, for example, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium, trisilicate, polyvinyl pyrrolidone, cellulose-based substances and polyethylene glycol. Adjuvants for topical or gel base forms may be selected from the group consisting of sodium carboxymethylcellulose, polyacrylates, polyoxyethylene-polyoxypropylene-block polymers, polyethylene glycol and wood wax alcohols.

Generally, the pharmaceutical compositions of this invention may be formulated and administered to the patient using methods and compositions similar to those employed for other pharmaceutically important agents. Any pharmaceutically acceptable dosage route, including, oral, topical, intranasal, or parenteral (including intravenous, intramuscular, subcutaneous, intracutaneous, periosteally, intra-articular, intrasynovial, intrathecal, intrasternal, intracranial or intralesional) may be used.

The pharmaceutical compositions of this invention may be provided in a variety of conventional depot forms. These include, for example, solid, semi-solid and liquid dosage forms, such as tablets, pills, powders liquid solutions, dilutions, suspensions, emulsions, liposomes, capsules, suppositories, injectable and infusible solutions. The preferred form depends upon the intended mode of administration and therapeutic application.

For example, oral administration of the pharmaceutical compositions of this invention may be by any orally acceptable dosage form including, but not limited to, capsules, tablets, and aqueous or non-aqueous suspensions, emulsions, oil dilutions and solutions. In the case of tablets for oral use, carriers which are commonly used include lactose and corn starch. Lubricating agents, such as magnesium stearate, are also typically added. For oral administration in a hard gelatin capsule form, useful diluents include lactose and dried corn starch. Soft gelatin capsules incorporating oils and/or polyethylene glycols excipients may also be used. When aqueous suspensions or emulsions are administered orally, the prodrug is combined with emulsifying and suspending agents. Flavoring, sweetening, or coloring agents may be added, if desired.

Preferably, the pharmaceutical compositions of this invention are formulated for oral administration. Even more preferred are oral emulsions comprising between about 5 to 40% (w/w) of the prodrug of Formula I (including the n-butyl ester specifically excluded from the compounds of this invention) and an ionic or non-ionic surfactant with the resulting composition having an HLB value of between 0–40. Preferred surfactants include Tween-20, Tween-80, Spam-20, Spam-40 and poloxamers, such as S-108.

According to another embodiment, the invention provides methods for treating a β-hemoglobinopathy in a patient. This method comprises the step of treating the patient with any of the compositions described above. The term "treating", as used herein includes reducing the severity, symptoms or effects of the β-hemoglobinopathy. Preferably, the method provides a serum butyric acid concentration of between about 0.03 mM and 3.0 mM within about 8 hours of administration. More preferably, this produces a plasma butyric acid concentration of between about 0.1 mM and 1.0 mM within about 6 hours of administration. Most preferably, the prodrug in the composition is present in an amount that produces a plasma butyric acid concentration of between about 0.1 mM and 1.0 mM within 2 hours of administration and the concentration remains within that range for at least 2 hours. These plasma levels are achieved by administering the prodrug of Formula I to the patient at a dose of between about 25–3000 mg/kg body weight one or more times per day. Preferably, the patient will be administered the prodrug between 1 and 4 times per day.

The β-hemoglobinopathies which may be treated by this method include sickle cell syndromes, such as sickle cell anemia, hemoglobin SC disease, hemoglobin SS disease and sickle β-thalassemia; β-thalassemia syndromes, such as β-thalassemia; other genetic mutations of the β-globin gene locus that lead to unstable hemoglobins, such as congenital Heinz body anemia, β-globin mutants with abnormal oxygen affinity and structural mutants of β-globin that result in thalassemic phenotype. These diseases are described in *The Molecular Basis of Blood Disease,* vol. II, G. Stamatoyannopoulos et at., eds., pp. 157–244 (1994).

According to a preferred embodiment, the above-described method comprises the additional step of treating the patient with an agent that is normally used to treat such β-hemoglobinopathies, for e.g., hydroxyurea. That agent may be administered prior to, sequentially with or after treatment with the butyrate prodrug-containing composition. Of course, if the composition used to treat the disease is one that already contains such conventional agent, this additional step can be omitted.

The amount of conventional agent administered in these methods is preferably less than that normally required to treat such diseases in a monotherapy. The normal dosages of these conventional agents are well known in the art. Such agents include hydroxyurea, clotrimazole, isobutyramide, erythropoietin and salts of short-chain fatty acids, such as phenylacetic acid, phenylbutyric acid and valproic acid. Preferably, the conventional agent used is hydroxyurea.

According to another embodiment, the invention provides method for treating diseases characterized by neoplastic, tumorigenic or malignant cell growth, as well as malignant hematological disorders. Treatment includes prevention of the progression the disease or its recurrence. Such diseases include carcinomas, myelomas, melanomas, lymphomas and leukemias. Preferably, the method provides the same serum butyric acid concentrations indicated above as being desirable for treating β-hemoglobinopathies.

According to a preferred embodiment, the above-described method comprises the additional step of treating the patient with an agent that is normally used to such malignancies. Preferably, that agent is hydroxyurea. That agent may be administered prior to, sequentially with or after treatment with the butyrate prodrug-containing composition. Of course, if the composition used to treat the disease is one that already contains such conventional agent, this additional step can be omitted.

The amount of conventional agent administered in these methods is preferably less than that normally required to treat such diseases in a monotherapy. The normal dosages of these conventional agents are well known in the art. Such agents include, erythropoietin, or cancer chemotherapeutic agents, such as hydroxyurea or 5-azacytidine. Hydroxyurea is a preferred conventional agent.

Combination therapies with conventional agents according to this invention (whether part of a single composition or administered separate from the prodrugs of this invention) may also exert an additive or synergistic effect, particularly when each component acts to treat or prevent the target disease via a different mechanism.

In order that the invention described herein may be more fully understood, the following examples are set forth. It should be understood that these examples are set forth for illustrative purposes only and are not to be construed as limiting this invention in any manner.

EXAMPLE 1

Synthesis of Compound IIIa and IIIb

We synthesized compound IIIa as follows. We combined 6.25 ml of methyl (S)-lactate with 13.75 ml of $Et_3N$ and then added that mixture to 50 ml of methylene chloride. We cooled this mixture to 0° C. in an ice bath and the slowly added 8.2 ml of butyryl chloride. This mixture was stirred overnight and then filtered through a Buchner filter. The precipitate cake was then washed with ether and the wash was combined with the filtrate. The organic layer from the filtrate was isolated, washed twice with water, once with brine and then dried over anhydrous $MgSO_4$. The crude yield was 12.48 g.

The material was then dissolved in 90% hexane/ethyl acetate and chromatographed on an MPLC column. Fractions containing the desired product were pooled and dried yielding 9.46 g of pure product. NMR analysis confirmed that the pure product was compound IIIa.

Compound IIIb was synthesized and purified in an identical manner, substituting methyl (R)-lactate for methyl (S)-lactate.

EXAMPLE 2

Synthesis of Compound IIIc

We synthesized compound IIIc by combining 7.4 ml of ethyl (S)-lactate with 13.75 ml of $Et_3N$ and then added that mixture to 50 ml of methylene chloride. We cooled this mixture to 0° C. in an ice bath and the slowly added 8.2 ml of butyryl chloride. This mixture was stirred overnight. TLC analysis of the mixture indicated incomplete reaction. We therefore added an additional 0.25 mole (2.5 ml) of butyryl chloride and allowed the reaction to continue with stirring for 24 hours.

The mixture was then filtered through a Buchner filter. The precipitate cake was then washed with ether and the wash was combined with the filtrate. The organic layer from the filtrate was isolated, washed twice with water, once with brine and then dried over anhydrous $MgSO_4$. The crude yield was 15.98 g.

The material was then dissolved in 90% hexane/ethyl acetate and chromatographed on an MPLC column. Fractions containing the desired product were pooled and dried yielding 9.97 g of pure product. NMR analysis confirmed that the pure product was compound IIIc.

EXAMPLE 3

Oral Availability of Butyrate Prodrugs of Lactic Acid in Rats

We evaluated oral bioavailability and sustenance of plasma concentrations of butyric acid in rats receiving either compound IIIa, IIIb or IIIc by oral gavage at doses of approximately 3 g/kg body weight. The butyrate prodrugs were formulated by simple dilution in corn oil.

The assay was carried out according to the protocols described in Daniel et al., *Clinica Chimica Acta*, 181, pp. 255–64 (1989); Planchon et al., *J. Pharm. Sci.*, 82, pp. 1046–48 (1993); Pouillart et al., *J. Pharm. Sci.*, 81, pp. 241–44 (1992)]. Each compound was tested in five to six rats (Sprague Dawley; Harlan Labs, Inc.) weighing approximately 300 grams each. The relevant $C_{max}$ for these agents are listed in Table 1, below.

TABLE 1

Pharmokinetics of butyrate prodrugs of lactic acid in rats

| Compound | Dose (g/kg) | No. of Animals | Butyrate $C_{max}$ (μM) | Butyrate $t_{max}$ (hr) | AUC (mM/hr) |
|---|---|---|---|---|---|
| IIIa | 2.7 | 4 | 1335 ± 593.2 | 0.56 ± 0.31 | 2.10 ± 0.42 |
| IIIb | 2.5 | 6 | 147.0 ± 119.1 | 0.54 ± 0.49 | 0.26 ± 0.14 |
| IIIc | 3.0 | 6 | 456.3 ± 80.7 | 1.71 ± 1.3 | 1.68 ± 0.16 |

These results demonstrate that the compounds of this invention are able to release butyrate at a suitable rate and provide a sufficient plasma concentration of butyrate to be utilized in the treatment of β-hemoglobinopathies and cancer.

EXAMPLE 4

Oral Availability of Butyrate Prodrugs of Lactic Acid in Monkeys

Compound IIIc was further tested in anemic rhesus monkeys. A single oral dose of compound IIIc (0.3, 1.0 or 3.0 g/kg body weight) diluted in corn oil was administered to the monkeys. The $C_{max}$ obtained at each of these doses is listed in Table II, below.

TABLE 2

Pharmacokinetic parameters for Compound IIIc in anemic rhesus monkeys

| Dose (g/kg) | No. of Animals | Butyrate $C_{max}$ ($\mu$M) | Butyrate $t_{max}$ (hr) | AUC (mM/hr) |
|---|---|---|---|---|
| 0.3 | 2 | 214.4 ± 88.8 | 0.75 | 0.30 ± 0.03 |
| 1.0 | 2 | 509.9 ± 90.9 | 3.0 | 1.33 ± 0.09 |
| 3.0 | 2 | 836.1 ± 88.4 | 4.0 | 3.41 ± 0.03 |

The time course of plasma butyric acid concentration following administration of the various doses of compound IIIc in individual monkeys is depicted in FIG. 1.

EXAMPLE 5

Efficacy Studies of Compound IIIc/Hydroxyurea Combination In Anemic Rhesus Monkeys The efficacy of compound IIIc administered in conjunction with hydroxyurea was tested on six anemic rhesus monkeys divided into three groups of two each. Each group was studied in two phases, as shown below. Fetal hemoglobin cells (F cells), Hemoglobin F level in total Hemoglobin (% Hb F) and % γ globin chain levels were monitored before and after each of the two phases. % F cells were measured according to the protocol described in Betke et al, *Blut.*, 4, pp. 241–9 (1958). % Hb F and % γ globin chain synthesis were measured using High Performance Liquid Chromatography (HPLC) according to the protocol described in Huisman, *J. Chromagtogr.*, 418, pp. 277 (1987).

TABLE 1

Phase I of the efficacy study

| Study Group | Number of Animals | Drug | Dose | Treatment Period |
|---|---|---|---|---|
| I | 2 | Hydroxyurea | 50 mg/kg/day | 5 weeks |
| II | 2 | Compound IIIc | 1 g/kg/day | 5 weeks |
| III | 2 | Compound IIIc | 3 g/kg/day | 6 weeks |

TABLE 2

Phase II of the efficacy study

| Study Group | Number of Animals | Drug | Dose | Treatment Period |
|---|---|---|---|---|
| I | 2 | Hydroxyurea + Compound IIIc | 50 mg/kg/day | 5 weeks |
| II | 2 | Compound IIIc | 1 g/kg/TID | 5 weeks |
| III | 2 | Compound IIIc | wash-out | 4 weeks |

Animal 1 in group I had a % F cell count of 8–10% before Phase I. At the end of Phase I the % F cell count in Animal 1 increased to 25%. At the end of Phase II the % F cell count in Animal 1 increased to 35%. Animal 2 in group II had a % F cell count of 8–10% before Phase I. At the end of Phase I the % F cell count in Animal 2 increased to 15%. At the end of Phase II the % F cell count in animal 2 increased to 22%. The increase in the % F cell count in Group I was accompanied by a measurable increase in the % Hb F and % γ-globin chain levels. Groups II and III showed a small but significant increase in % F cells with no measurable change in HbF or γ-globin chain levels.

In all three groups, there was no detectable difference in the levels of the triglycerides and ALT prior to or during the two phases of the efficacy study.

The results demonstrated the utility of the butyrates of the present invention, when used in conduction with conventional agents, such as hydroxyurea, for inducing fetal hemoglobin in β-hemoglobinopathies.

While we have hereinbefore described a number of embodiments of this invention, it is apparent that our basic constructions can be altered to provide other embodiments which utilize the syntheses, processes and compositions of this invention. Therefore, it will be appreciated that the scope of this invention is to be defined by the claims appended hereto rather than by the specific embodiments which have been presented hereinbefore by way of example.

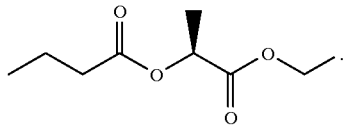

We claim:

1. A method for increasing fetal hemoglobin production in a patient comprising the step of administering to said patient a pharmaceutical composition comprising:

a. an amount of a butyrate prodrug of Formula I:

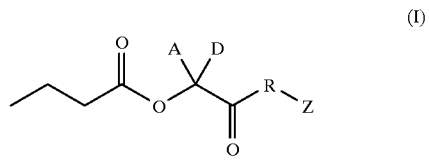

(I)

effective to increase fetal hemoglobin; wherein:

A and D are independently selected from the group consisting of hydrogen, carbocyclylalkoxyalkyl or C(1–4)-straight or branched alkyl, C(2–4)-straight or branched alkenyl or alkynyl, which may be independently substituted with hydroxy, alkoxy, carboxyalkyl, alkylamido, arylamido, heterocyclylamido, aralkylamido, heterocyclylalkylamido, alkoxycarbonylamino, alkenoxycarbonylamino, carbocyclyloxycarbonylamino, heterocyclyloxycarbonylamino, carbocyclylalkoxycarbonylamino, heterocyclylalkoxycarbonylamino, alkoxyalkoxycarbonylamino, amino, amido, carboxyl, thiol, thiomethyl, thiophenyl, aryl and heterocyclyl; provided that A and D are not simultaneously hydrogen;

R is O, NH, NC(1–5)-straight or branched alkyl or NC(2–5)-straight or branched alkenyl, any of which may be optionally substituted with a carbocyclyl or heterocyclyl moiety;

Z is hydrogen, C(1–4)-straight or branched alkyl, C(2–4)-straight or branched alkenyl or alkynyl, carbocyclyl, or heterocyclyl, any of which may be optionally substituted with 1 or 2 groups independently chosen from C(1–3)-alkyl, C(2–3)-alkenyl or alkynyl, alkoxy, alkenoxy, alkynoxy, amido, thioalkyl, carbocyclyl or heterocyclyl; and each stereogenic carbon may be in the R or S configuration; and b. a pharmaceutically acceptable adjuvant or carrier.

2. A method for stimulating cell differentiation in a patient comprising the step of administering to said patient a pharmaceutical composition comprising:

a. an amount of a butyrate prodrug of Formula I:

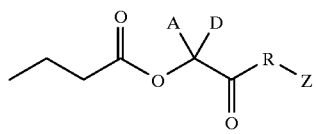
(I)

effective to promote cell differentiation; wherein:

A and D are independently selected from the group consisting of hydrogen, carbocyclylalkoxyalkyl or C(1–4)-straight or branched alkyl, C(2–4)-straight or branched alkenyl or alkynyl, which may be independently substituted with hydroxy, alkoxy, carboxyalkyl, alkylamido, arylamido, heterocyclylamido, aralkylamido, heterocyclylalkylamido, alkoxycarbonylamino, alkenoxycarbonylamino, carbocyclyloxycarbonylamino, heterocyclyloxycarbonylamino, carbocyclylalkoxycarbonylamino, heterocyclylalkoxycarbonylamino, alkoxyalkoxycarbonylamino, amino, amido, carboxyl, thiol, thiomethyl, thiophenyl, aryl and heterocyclyl; provided that A and D are not simultaneously hydrogen;

R is O, NH, NC(1–5)-straight or branched alkyl or NC(2–5)-straight or branched alkenyl, any of which may be optionally substituted with a carbocyclyl or heterocyclyl moiety;

Z is hydrogen, C(1–4)-straight or branched alkyl, C(2–4)-straight or branched alkenyl or alkynyl, carbocyclyl, or heterocyclyl, any of which may be optionally substituted with 1 or 2 groups independently chosen from C(1–3)-alkyl, C(2–3)-alkenyl or alkynyl, alkoxy, alkenoxy, alkynoxy, amido, thioalkyl, carbocyclyl or heterocyclyl; and each stereogenic carbon may be in the R or S configuration; and b. a pharmaceutically acceptable adjuvant or carrier.

3. The method according to claim 1, wherein said method is used for treating a β-hemoglobinopathy in said patient.

4. The method according to claim 3, comprising the additional step of administering to said patient a conventional agent for treating a β-hemoglobinopathy.

5. The method according to claim 3, comprising the additional step of administering to said patient hydroxyurea.

6. The method according to claim 2, wherein said method is used for treating a malignant disease in said patient.

7. The method according to claim 6, comprising the additional step of adminstering to said patient a conventional agent for treating a malignant disease.

8. The method according to claim 6, comprising the additional step of adminstering to said patient hydroxyurea for treating a malignant disease in a patient.

9. The method according to claim 4 wherein said conventional agent is hydroxyurea.

10. The method according to claim 9, wherein the butyrate prodrug is compound (IIIc).

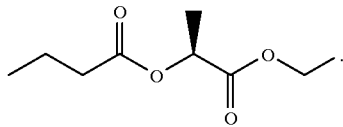

11. The method according to claim 7 wherein said conventional agent is hydroxyurea.

12. The method according to claim 11 wherein the butyrate prodrug is compound (IIIc).